United States Patent
Sasakura

(10) Patent No.: US 6,190,166 B1
(45) Date of Patent: Feb. 20, 2001

(54) ORTHODONTIC DEVICE

(76) Inventor: Hitoshi Sasakura, 4-612-1 Sekiyatamachi, Niigata-shi, Niigata-ken (JP)

(*) Notice: Under 35 U.S.C. 154(b), the term of this patent shall be extended for 0 days.

(21) Appl. No.: 09/450,654

(22) Filed: Nov. 30, 1999

(30) Foreign Application Priority Data

Jan. 28, 1999 (JP) .................................................. 11-019819

(51) Int. Cl.$^7$ .................................................. A61C 3/00
(52) U.S. Cl. .................................. 433/14; 433/11; 433/20
(58) Field of Search .................................. 433/14 OR, 11, 433/20

(56) References Cited

U.S. PATENT DOCUMENTS

| | | | |
|---|---|---|---|
| 1,280,628 | * 10/1918 | Angle | 433/14 |
| 3,477,129 | * 11/1969 | Rubin | 433/11 |
| 4,310,306 | * 1/1982 | Wallshein | 433/14 |
| 4,496,318 | * 1/1985 | Connelly, Jr. | 433/14 |
| 4,669,980 | * 6/1987 | Degnan | 433/17 |

FOREIGN PATENT DOCUMENTS

| | | |
|---|---|---|
| 55-48814 | 12/1980 | (JP) . |
| 61-47097 | 10/1986 | (JP) . |
| 2-53053 | 11/1990 | (JP) . |
| 3-71896 | 11/1991 | (JP) . |

* cited by examiner

Primary Examiner—John J. Wilson
(74) Attorney, Agent, or Firm—Wenderoth, Lind & Ponack, L.L.P.

(57) ABSTRACT

An orthodontic device includes a wire member and a fixing member. The wire member consists of on arch wire fixed through concatenation with a tooth and an engaging part fixed at positions corresponding to the points of fixation of the arch wire. The fixing member 2 fixed on the tooth is provided with a mounting groove for mounting the engaging part.

4 Claims, 3 Drawing Sheets

ORTHODONTIC DEVICE

BACKGROUND OF THE INVENTION

1. Field of the Invention

This invention relates to an orthodontic device to be used for correcting teeth in the state of irregular articulation.

2. Description of a Prior Art

As orthodontic means, it has been heretofore customary to connect adjacent teeth with a wire so as to ensure the exertion of force on teeth under correction in the direction of correction. A concrete device for embodying this means comprises an arch wire and a fixing member to be fastened to the relevant tooth. The fixing member has formed therein a wire mounting groove. The force of correction is enabled to act on the tooth under correction by fixing the stationary position of the arch wire in the mounting groove.

As means for fixing the aforementioned arch wire in the mounting groove, use of a rock pin (JP-B-55-48814), an insertion groove (JP-B-61-47097), or a binding line (JP-B-02-53053 and JP-B-03-71896) has been proposed.

The conventional mounting structure mentioned above has the arch wire directly fixed unexceptionally to the fixing member fastened to the tooth and has this work of fixing performed, as a matter of course, while the patient under treatment keeps his mouth open. Moreover, since the mounting of the arch wire requires this wire to be fixed so as to produce a proper amount of correcting force, the dentist himself finds it a good deal of work and the patient finds it a labor accompanied by considerable pain. The four prior patent publications disclose inventions which invariably move the arch wire toward and from the mounting groove for attachment and detachment on the tooth in the direction from the horizontal direction relative to the tooth or from the root toward the tip of the tooth. When the orthodontic device is operated particularly on the rear side of a tooth, the attachment or detachment of the wire to the mounting groove inside the narrow oral cavity turns out to be troublesome work.

Though the conventional dental correction resorting to the arch wire utilizes the bend or the twist to be produced in the arch wire for adjusting the direction of the correcting force exerted on the tooth, this method does not necessarily allow the adjustment to be attained with expected delicacy.

A main object of this invention, therefore, is to provide an orthodontic device which permits the work of mounting to be effected on the patient easily and, at the same time, allows the adjustment the correcting force to be finely carried out.

SUMMARY OF THE INVENTION

The orthodontic device according to this invention comprises a wire member consisting of on arch wire fixed through concatenation with a tooth and an engaging part fixed at positions corresponding to points of fixation of the arch wire, and a fixing member adapted to be fixed to the tooth and provided with means for mounting the engaging part.

The arch wire, therefore, can be fixed through concatenation to the patient's tooth by having the fixing member mounted fast in advance at prescribed positions of the patient's tooth as with adhesive agent, forming the engaging part on the arch wire at the positions and in the direction to be selected preparatorily in due consideration of the expected action of the correcting force, and mounting the engaging part on the fixing member.

Further, in the orthodontic device according to the present invention, the engaging part of the wire member is projected in the shape of a leg from the arch wire and provided with a pair of opposite leg parts that are endowed with elasticity so as to resist closing of the leg parts. The leg parts provided with engaging projected parts projecting outwardly, and the fixing member is provided with a mounting groove possessing inclined inner side faces allowing insertion of the engaging projected parts and a wire groove for enabling the arch wire to be set therein after the leg has been forcibly inserted into the mounting groove and the engaging projected parts have been brought into engagement with a terminal of the mounting groove.

When the leg-shaped engaging part is forcibly inserted into the mounting groove, therefore, the leg parts are gradually pressed in the width direction by the inclined inner side faces. When the engaging projected parts depart from the mounting groove, the leg parts are allowed to open by the elastic force of themselves, and the engaging projected parts are brought into engagement with the terminal of the groove and induced to assume a state no longer allowed to slip and, at the same time, the arch wire is set fast in the wire groove and fixed through concatenation with the patient's tooth.

The above and other objects and features of this invention will be described more specifically below with reference to the drawings annexed hereto.

DETAILED DESCRIPTION OF THE PREFERRED EMBODIMENTS

Now, embodiments of the orthodonic device according to this invention will be described below.

Figure 1:
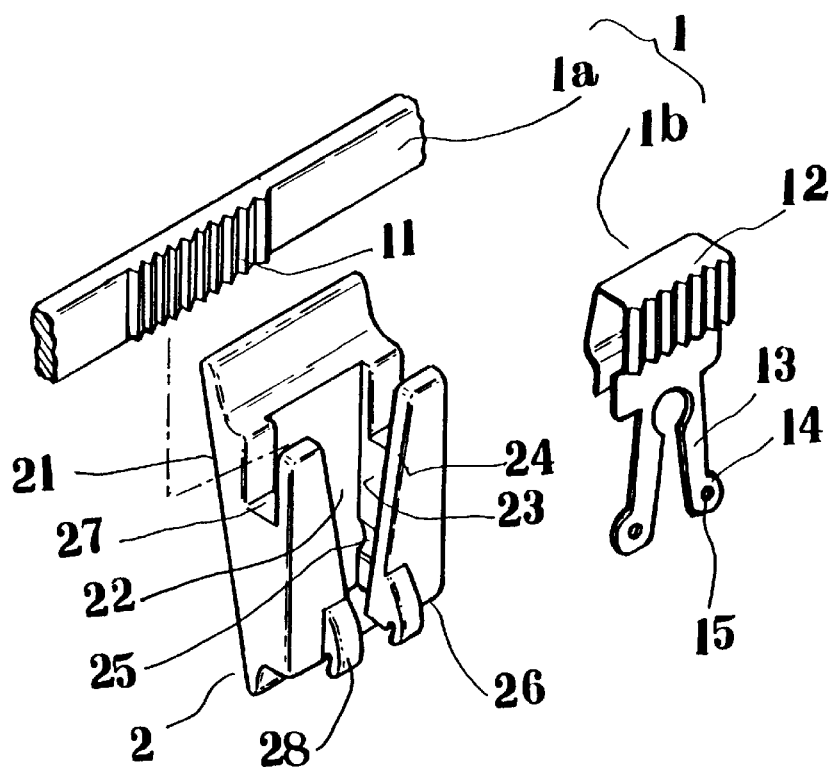
FIG. 1 is an exploded perspective view of an orthodontic device according to one embodiment of this invention.
Figure 2:
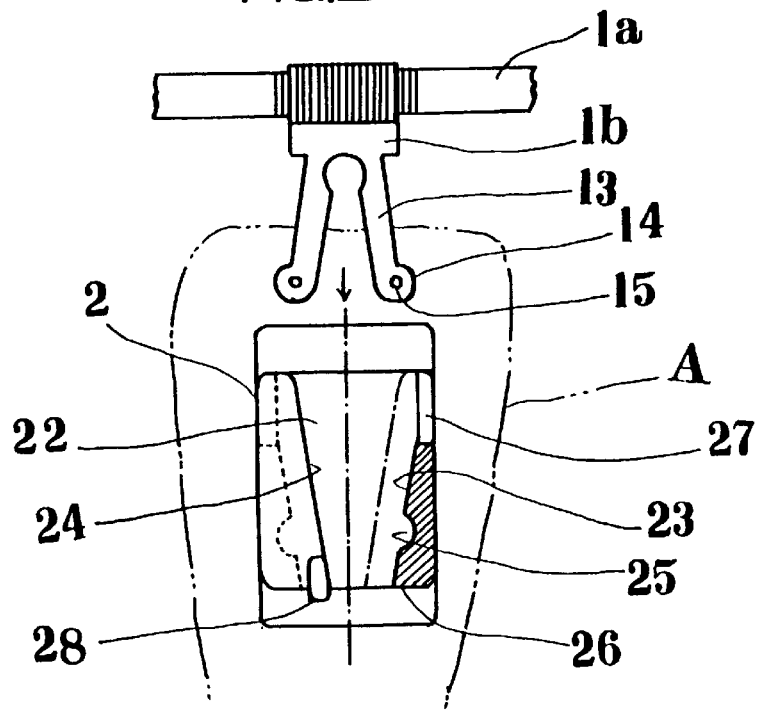
FIG. 2 is a front view of the device in a state ready for mounting.

One embodiment of the orthodontic device illustrated in FIG. 1 and FIG. 2 comprises a wire member 1 and a fixing member 2 to be fixed to a given tooth. The component members 1 and 2 can be used for either the upper tooth or the lower tooth. This embodiment refers to the case of the lower tooth.

The wire member 1 consists of an arch wire 1a and an engaging part 1b. The arch wire 1a, though equaling the arch wire used in the conventional orthodontic device, is provided with means for fixing the engaging part 1b to inhibit lateral motion. In the present embodiment, the means comprises a horizontally corrugated part 11 formed on the lateral surface of the arch wire 1a.

The engaging part 1b, which is formed of a thin plate, is hung down from the position corresponding to the point of the arch wire 1a fixed by concatenation to the tooth A. It is provided in the upper part thereof with a fitting part 12 and in the lower part thereof with a leg. The fitting part 12 has the shape of a clip fit for hugging the arch wire 1a and forms a corrugating part corresponding to the horizontally corrugated part 11 and serves the purpose of fixing the engaging part 1b at the prescribed position of the arch wire 1a. After the position and the angle of fixation of the engaging part 1*b* to the arch wire 1*a* are determined, they are fixed to each other as by soldering.

The leg is shaped so as to have laterally opposite leg parts 13 extending downwardly and is endowed with elastic force sufficient for the laterally opposite leg parts 13 to generate a fully satisfactory repulsive force when they are pressed toward each other. It is provided at the lower terminals of the leg parts 13 with laterally opposite engaging parts 14 projecting outwardly. The engaging projected parts 14 are each provided with a manipulating hole 15. The engaging projected parts 14 have the degree of projection thereof given due consideration lest difficulty should be encountered in the operation of their insertion into a mounting groove, which will be specifically described herein below.

The fixing member 2 is integrally formed in the shape of a block by precision casting or with a resinous material. It is produced as a set of several kinds for use respectively with front teeth, molars, and canine teeth. It is provided on one side thereof with a fitting face 21 intended to be opposed and fastened to a tooth A and on the side opposite to the fitting face 21 with a vertically penetrating mounting groove 22. The mounting groove 22 has opposed inclined inner side faces 23 thereof allowing insertion of the engaging projecting parts 14. Blocking parts 24 are shaped like hoods extending from the outer portions of the inner side faces 23 to the center therebetween lest the leg parts should slip off externally in the front and the rear direction or the leg parts 13 should produce a backlash lengthwise in the mounting groove 22. Halfway along the lengths of the inclined inner side faces, depressed parts 25 for taking hold of the engaging projecting parts 14 are produced.

Further, the fixing member 2 is provided in the upper face thereof with a wire groove 27 adapted to be fitted with the arch wire 1*a* after the leg parts 13 have been inserted into the mounting groove 22 and the engaging projected parts 14 have been thrust toward the opposite lower end faces (engagement receiving part 26) of the mounting groove 22. It is also provided at lower suitable positions with tying projected parts 28.

Figure 3A:
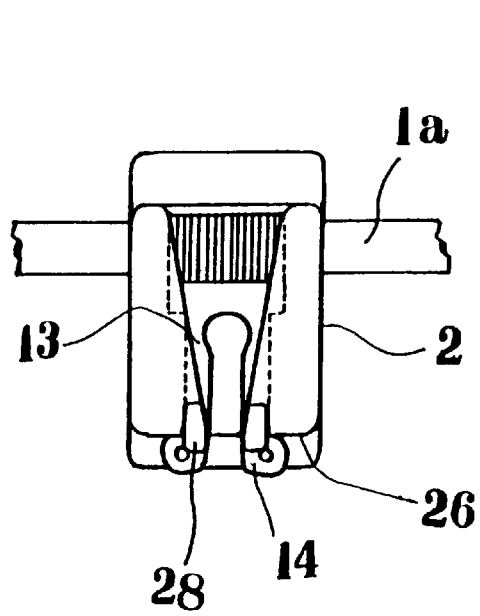
FIGS. 3(A) and 3(B) illustrate a the device in a state during the process of mounting, FIG. 3(A) depicting the front view and FIG. 3(B) the side view.
Figure 3B:
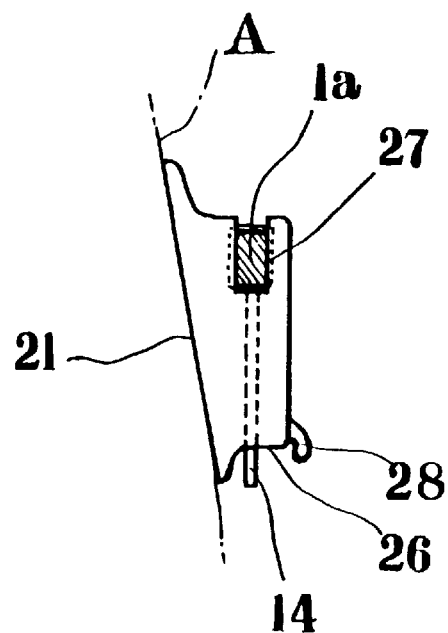

Then, the fixing member 2 is fixed, as with an adhesive agent, at a prescribed position on a given tooth A and the leg parts 13 of the engaging part 1*b* of the wire member 1 are inserted into the mounting groove 22. The leg parts 13 leave a gap therebetween, narrowed in consequence of the descent of the engaging projecting parts 14 along the inclined inner side faces 23. When the engaging projected parts 14 thrust through the mounting groove 22, the pressure of the narrowed gap is relieved and the elastic force of the leg parts 13 opens themselves in the opposite lateral directions, with the result that the engaging projected parts 14 will be brought into engagement with the engagement receiving parts 26 and the wire member 1 will be mounted on the fixing member 2 as illustrated in FIG. 3. Since the arch wire 1*a* is simultaneously fitted in the wire groove 27, the wire member 1 and the fixing member 2 are integrated with added thoroughness.

By preparatorily fastening the fixing member 2 to the patient's tooth and fixing the engaging part 1*b* at a prescribed position to the arch wire 1*a*, with due consideration to the direction of correction, and, as occasion demands, imparting a bend (lengthwise and bilaterally) and a twist delicately to the leg parts 13 of the engaging part 1*b*, therefore, simply the forced insertion of the engaging part 1*b* into the mounting groove 22 suffices to attain the mounting of the arch wire 1*a* in the oral cavity. Moreover, since this mounting is invariably produced in the vertical direction relative to the tip of a tooth, the work of mounting becomes very easy and, at the same time, the burden on the patient during the process of correction is lightened.

The point at which the correcting force of the arch wire 1*a* acts is not limited to the wire groove 27 but is likewise attained between the leg parts 13 and the mounting groove 22. Thus, the correcting force generated by the arch wire 1*a* acts throughout the whole of the fixing member 2 and, therefore, the correction can be implemented efficiently and precisely.

Figure 4A:
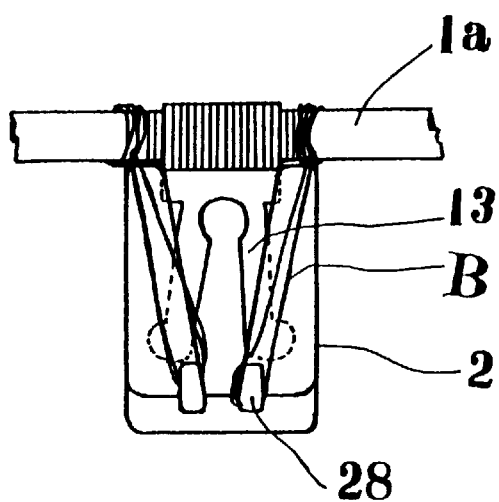
FIGS. 4(A) and 4(B) illustrate the device in the state during the process of tacking, FIG. 4(A) depicting the front view and FIG. 4(B) the side view.
Figure 4B:
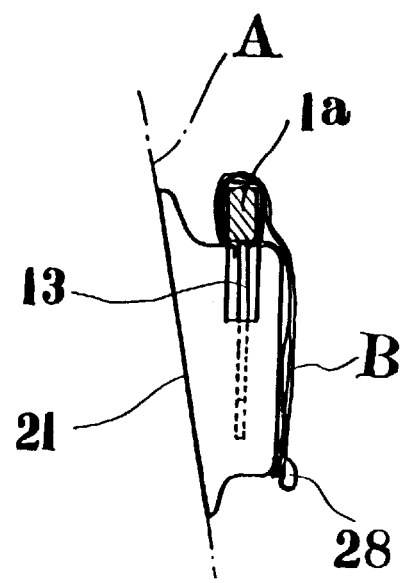

During the course of an orthodontic treatment, the correction can be attained gradually by imparting alterations to the point of attachment of the engaging part 1*b* to the arch wire 1*a* in the wire member 1 and altering the wire member 1 in the formation of the arch wire 1*a* in shape without producing any change in the fixing member 2. The work of removal after the mounting can be easily implemented by simply inserting the leading terminals of a tool like pincers into the manipulating holes 15, nipping the leg parts 13 with the tool, and pulling the tool upwardly to extract the leg parts 13. Further, the tacked state can be produced by setting the engaging projected parts 14 in place in the depressed parts 25 of the inclined inner side faces as illustrated in FIG. 4. Moreover, when the wire member 1 is tied fast to the fixing member 2 with a tying line B by making effective use of tying projected parts 28, they can be tacked by dint of intimacy prior to the mounting which is fated to impart a strong correcting force.

Figure 5:
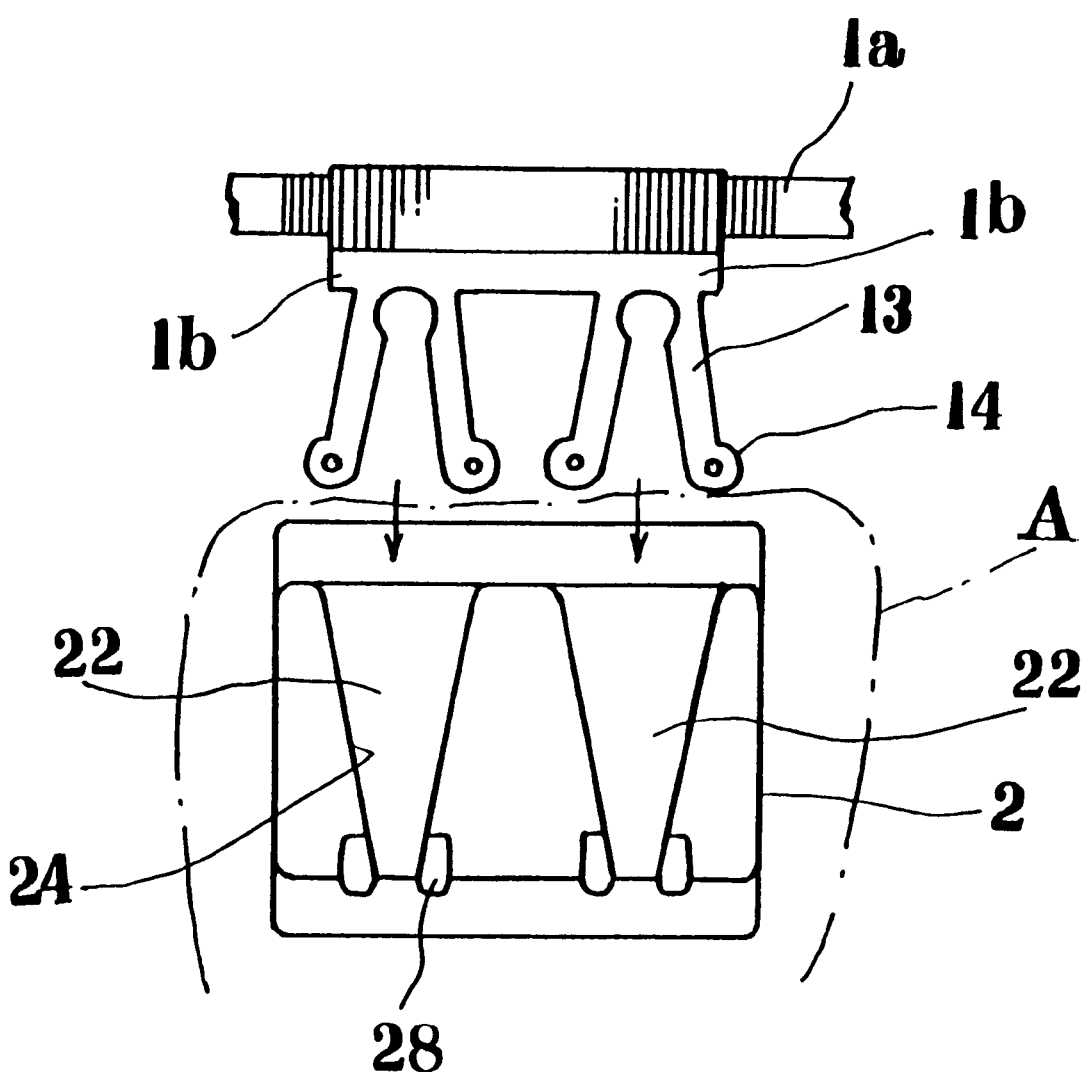
FIG. 5 is a front view illustrating another embodiment of the invention.

This invention allows the wire member 1 and the fixing member 2 to be effectively applied no matter whether the arch wire 1*a* is used on the front side (lip side) or on the rear side (tongue side) and only requires the wire member 1 and the fixing member 2 to be formed on the side on which the arch wire 1*a* is mounted. The engaging part 1*b* and the mounting groove 22 do not need to be solely used for each tooth. In the case of a tooth of large width, such as a back tooth, a combination of two parallelly arranged engaging parts 1*b* and a mounting mechanism as illustrated in the embodiment of FIG. 5 may be alternatively adopted.

Further, the specific construction of each component part does not need to be restricted to the embodiments described above. The means for fixing the engaging part 1*b* of the wire member 1, for example, may be the insertion of a pin in a through hole formed at a prescribed position of the arch wire 1*a* or by soldering. The fixing member 2 may be constructed by combining separate segments instead of being a one-piece block. The mounting groove 22 may be formed in the shape of a cylinder with a vertically penetrating hole instead of being provided with the blocking parts 24 of the shape of a hood.

This invention, as described above, concerns an orthodontic device which comprises the wire member and the fixing member, operates by the principle that the wire member fixes the engaging part at positions corresponding to the points of fixation through concatenation between the arch wire and a given tooth, and requires the fixing member fixed on the tooth to be provided with means for mounting the engaging part. This invention, consequently, curtails the time to be spent for the work of correction and alleviates the physical burden to be exerted on the patient during the work of mounting the arch wire by facilitating the work of mounting the arch wire, and permits fine adjustment of the amount of correction in the direction of action and realizes accurate movement of the tooth by finely adjusting the shape of the engaging part.

What is claimed is:

1. An orthodontic device comprising:
    a wire member comprising an arch wire, said arch wire having points of fixation there along, and an engaging part fixed at one of said points of fixation of said arch wire, said engaging part comprising a leg projecting from said wire member and comprising a pair of opposite leg parts that are elastic so as to tend to resist said leg parts being, brought toward each other, and said leg parts having outwardly projected engaging parts; and a fixing member adapted to be fixed to a tooth, said fixing member having a mounting groove with inclined inner side faces that allow insertion of said engaging projected parts and a wire groove for enabling said arch wire to be set therein after said leg has been forcibly inserted into said mounting groove and said engaging projected parts have been brought into engagement with an end of said mounting groove.

2. The orthodontic device of claim 1, wherein said fixing member comprises depressions positioned halfway along a length of said inclined inner side faces for temporarily stopping said engaging projected parts and tying projected parts at a lower position than said depressions.

3. The orthodontic device of claim 1, wherein said engaging part further comprises a fitting part formed as a clip, said fitting part and said arch wire, at said points of fixation, having respective corresponding corrugations.

4. The orthodontic device of claim 1, wherein said fixing member has blocking parts extending from outer parts of said inclined inner side faces so as to at least partially block said mounting groove from a front side of said fixing member to prevent said leg parts from slipping out of said mounting groove toward the front side.

* * * * *